United States Patent [19]

Weber et al.

[11] Patent Number: 5,182,400
[45] Date of Patent: Jan. 26, 1993

[54] PROCESS FOR THE PREPARATION OF ESTERS OF 5-ALKYLPYRIDINE-2,3-DICARBOXYLIC ACID

[75] Inventors: Jurgen Weber, Oberhausen; Peter Lappe, Dinslaken; Helmut Springer, Oberhausen, all of Fed. Rep. of Germany

[73] Assignee: Hoechst Aktiengesellschaft, Fed. Rep. of Germany

[21] Appl. No.: 741,603

[22] Filed: Aug. 7, 1991

[30] Foreign Application Priority Data

Aug. 8, 1990 [DE] Fed. Rep. of Germany ....... 4025076

[51] Int. Cl.$^5$ ................. C07D 213/55; C07D 213/69; C07D 213/803
[52] U.S. Cl. .................................... 546/250; 546/321
[58] Field of Search ................................ 546/250, 321

[56] References Cited

U.S. PATENT DOCUMENTS 4,973,695 11/1990 Yamashita et al. ................. 546/250

Primary Examiner—C. Warren Ivy
Assistant Examiner—P. G. Spivack
Attorney, Agent, or Firm—Jordan B. Bierman

[57] ABSTRACT

Process for the preparation of 5-alkylpyridine-2,3-dicarboxylic esters by reaction of 2-oxosuccinic esters with 2-alkylacrolein oximes.

15 Claims, No Drawings

PROCESS FOR THE PREPARATION OF ESTERS OF 5-ALKYLPYRIDINE-2,3-DICARBOXYLIC ACID

This Application claims the benefit of the priority of German 40 25 076.8, filed Aug. 8, 1990.

The invention relates to a process for the preparation of esters of 5-alkylpyridine-2,3-dicarboxylic acid by reaction of 2-alkylacrolein oximes with 2-oxosuccinic esters.

BACKGROUND OF THE INVENTION

Derivatives of pyridine-2,3-dicarboxylic acid, in particular 5-alkylpyridine-2,3-dicarboxylic acids, are valuable intermediates for the preparation of 2-(2-imidazolin-2-yl)nicotinic acid compounds, which have distinct herbicidal activity. In particular, the (R,S)-5-ethyl-2-(4-isopropyl-4-methyl-5-oxo-2-imidazoline-2-yl)nicotinic acid is of economic interest. The preparation of this compound is described, for example, in U.S. Pat. No. 4,460,776.

In accordance with their importance, a number of syntheses are known for the preparation of pyridine-2,3-dicarboxylic acid derivatives. According to the teaching of EP 274,379 A2, compounds of pyridine-2,3-dicarboxylic acid are obtained either by reaction of 3-halogeno-2-ketosuccinic acids with α,β-unsaturated aldehydes or ketones and ammonia, or from aminobutenedicarboxylic esters and α, β-unsaturated aldehydes or ketones. These process either start from halogen-containing compounds, which require the use of halogen-resistant apparatuses and lead to halogen compounds polluting the environment as waste products, or from commercially unavailable or insufficiently available substances. Their use is therefore limited.

The synthesis of pyridine-2,3-dicarboxylic acid derivatives described in EP 299,362 A1 is also based on the use of aminobutenedicarboxylic esters and α, β-unsaturated carbonyl compounds. Both starting materials have to be used in pure form. The high expenditure for distillation resulting from this requirement casts doubt on the economy of the process.

The process of EP 308,084 A1 for the preparation of pyridine derivatives starts from halogenopropenoic or halogenobutenoic acid derivatives which are reacted with a 2-alkylacrolein oxime. An example of this synthesis is the preparation of 5-ethylpyridine-2,3-dicarboxylic acid from N-phenylchloromaleinimide and 2-ethylacrolein oxime. Apart from the fact that N-phenylchloromaleinimide can only be obtained by a complicated sequence of several reaction steps from maleic anhydride, the process requires long reaction times of up to 60 hours and gives the desired compound only in moderate yields.

As can be seen, the known processes do not fulfill all industrial and economical conditions which have to be satisfied by industrially performed processes. In some cases, they are based on the use of starting materials whose preparation is complicated or which lead to by-products polluting the environment during the synthesis, or further processing and, in other cases, they require long reaction times or give the desired compounds only in insufficient yields.

The aim of the present invention is to remove the disadvantages of the prior art and to provide a process for the preparation of esters of 5-alkylpyridine-2,3-dicarboxylic acid which satisfies the requirements of industrial practice.

SUMMARY OF THE INVENTION

The invention is directed to in a process for the preparation of esters of 5-alkylpyridine-2,3-dicarboxylic acid. It comprises reacting 2-oxosuccinic esters in the presence of acid catalysts with 2-alkylacrolein oximes. The starting materials for the process according to the invention are commercially available substances or substances which are easily derived from commercially available base chemicals by known methods.

Of the oxosuccinic esters (oxalacetic esters), diethyloxosuccinate is the best known. It is synthesized from diethyl oxalate and ethyl acetate by Claisen condensation in the presence of sodium alcoholate. Other esters, including mixed ones, are available in the same manner from the corresponding esters of oxalic acid and acetic acid. In accordance with the process according to the invention, free diesters can be used. The same good results are obtained by starting from the alkali metal salt of the enol form of the diesters, and converting it into the enol by reaction with an equivalent amount or a slight excess of an acid, advantageously a mineral acid.

The 2-alkylacrolein oximes are obtained in a known manner from aldehydes and hydroxylamine salts. Alkylacroleins are obtained by aldol condensation of saturated aliphatic aldehydes with formaldehyde, for example in the presence of a catalyst system comprising secondary amines and an aliphatic carboxylic acid. 2-Ethylacrolein is obtained, for example, in this manner from n-butyraldehyde and formaldehyde. According to the invention, alkylacrolein oximes in which the alkyl radical contains one to ten carbon atoms and is straight or branched chain are used.

The process according to the invention can be carried out in a simple manner by mixing the two reactants in the presence of an acid catalyst, if appropriate at elevated temperature. It is advantageous, but not absolutely necessary, to carry out the reaction in an inert solvent. This reaction variant is used whenever the starting materials are not free oxosuccinic diesters but their alkali metal enolates. In this case, the aqueous solution of the alkali metal compound is reacted with the acid and the diester is extracted by means of an inert solvent. The solution thus obtained is then reacted with the 2-alkylacrolein oxime. Suitable solvents for the reactions are alcohols, such as butanol, ethylene glycol; esters, for example ethyl acetate; halogenated hydrocarbons, for example chloroform or carbon tetrachloride; and aromatic hydrocarbons such as benzene, toluene or xylene. The diester concentration is advantageously 10 to 50% by weight, based on the solution.

The addition of a catalyst to the reaction mixture shortens the reaction time and suppresses undesired side reactions. The compounds which serve as catalysts are acid compounds, such as strong inorganic acids, for example sulfuric acid and hydrochloric acid; organic sulfonic acids, for example methanesulfonic acid and p-toluenesulfonic acid; and organic carboxylic acids, for example acetic acid. Organic sulfonic acids are preferred. The amount of catalyst is 0.01 to 0.2, preferably 0.05 to 0.1, mole of acid per mole of diester.

2-Alkylacrolein oxime is added in portions, undiluted or dissolved in the same solvent as the diester, to the diester solution containing the catalyst. The reactants can be used in a molar ratio of 1:1. However, it is recommended to use one of the two reactants in excess for which a molar ratio of diester to oxime of 1:2 to 2:1 has proved suitable.

The reaction of the starting materials is carried out at elevated temperature. It depends on the solvent and catalyst selected. The temperature range chosen is usually between 50° and 150° C., preferably 80° to 100° C. Higher temperaturs should be avoided due to the thermal instability of the oxime. After the reaction is complete, which require 4 to 10 hours (depending on the reaction temperature), the 5-alkylpyridine-2,3-dicarboxylic acid derivative is isolated from the reaction mixture and purified using conventional methods. Suitable methods are extraction with a solvent, distillation, recrystallization and chromatography. According to the invention, 5-alkylpyridine-2,3-dicarboxylic esters are obtained in high yield and high purity after a short reaction time from low-cost and readily available starting materials.

The invention is illustrated in more detail by the examples which follow, but is not to be limited thereby.

EXAMPLE 1

740 g of toluene, 250 g of water, and 117 g of (32%) hydrochloric acid are initially introduced into a 2 liter round-bottom flask, and 209.5 g of the sodium salt of diethyl 2-oxosuccinate is added at 25° C. within 5 minutes. After a reaction time of 1 hour at 25° C., phase separation takes place.

The organic phase (924.3 g) is heated to 65° C. after addition of 9.36 g of p-toluenesulfonic acid, and 141.8 g of 2-ethylacrolein oxime (purity 90.8%) is added dropwise at this temperature within 15 minutes. After a reaction time of 7 hours at 84° to 90° C., the mixture is allowed to cool to room temperature, the organic phase (1056.1 g) is separated from the water phase and washed three times with 300 g of water each time.

The organic phase after washing (1021.2 g) is freed of the solvent in the vacuum of an aspirator at a bath temperature of 95° C. According to GLC analysis, the residue (261.1 g) contains 43.9% diethyl 5-ethylpyridine-2,3-dicarboxylate, which corresponds to a yield of 45.7% of theoretical based on the sodium salt of diethyl 2-oxosuccinate used.

EXAMPLE 2

740 g of xylene, 250 g of water, and 117 g of (32%) hydrochloric acid are initially introduced into a 2 liter round-bottom flask, and 209.5 g of the sodium salt of diethyl-2-oxosuccinate is added at 25° C. within 5 minutes. After a reaction time of 1 hour at 25° C., phase separation takes place.

The organic phase (922.7 g) is heated to 65° C. after addition of 9.36 g of p-toluenesulfonic acid, and 141.8 g of 2-ethylacrolein oxime (purity 90.8%) is added dropwise at this temperature within 15 minutes. After a reaction time of 7 hours at 90° to 97° C., the mixture is allowed to cool to room temperature, the organic phase (1058.7 g) is separated from the water phase and washed three times with 300 g of water each time.

The organic phase after washing (1017.6 g) is freed of the solvent in the vacuum of an aspirator at a bath temperature of 95° C. According to GLC analysis, the residue (233.4 g) contains 45.5% of diethyl 5-ethylpyridine-2,3-dicarboxylate, which corresponds to a yield of 42.3% of theoretical, based on the sodium salt of diethyl 2-oxosuccinate used.

EXAMPLE 3

740 g of toluene, 250 g of water, and 117 g of (32%) hydrochloric acid are initially introduced into a 2 liter round-bottom flask, and 209.5 g of the sodium salt of diethyl 2-oxosuccinate is added at 25° C. within 5 minutes. After a reaction time of 1 hour at 25° C., phase separation takes place.

The organic phase (925.2 g) is heated to 65° C. after addition of 18.7 g of p-toluenesulfonic acid, and 141.8 g of 2-ethylacrolein oxime (90.8% pure) are added dropwise at this temperature within 15 minutes. After a reaction time of 7 hours at 86° to 91° C., the mixture is allowed to cool to room temperature, the organic phase (1055.4 g) is separated from the water phase and washed three times with 300 g of water each time.

The organic phase after washing (1014.2 g) is freed of the solvent in the vacuum of an aspirator at a bath temperature of 95° C. According to GLC analysis, the residue (245.7 g) contains 53.2% of diethyl 5-ethylpyridine-2,3-dicarboxylate, which corresponds to a yield of 52.1% of theoretical, based on the sodium salt of diethyl 2-oxosuccinate used.

EXAMPLE 4

740 g of toluene, 250 g of water, and 117 g of (32%) hydrochloric acid are initially introduced into a 2 liter round-bottom flask, and 209.5 g of the sodium salt of diethyl 2-oxosuccinate is added at 25° C. within 5 minutes. After a reaction time of 1 hour at 25° C., phase separation takes place.

The organic phase (924.5 g) is heated to 65° C. after addition of 9.4 g of p-toluenesulfonic acid, and 130.9 g of 2-ethylacrolein oxime (90.8% pure) are added dropwise at this temperature within 15 minutes. After a reaction time of 7 hours at 84° to 89° C., the mixture is allowed to cool to room temperature, the organic phase (1053.2 g) is separated from the water phase and washed three times with 300 g of water each time.

The organic phase after washing (1018.6 g) is freed of the solvent in the vacuum of an aspirator at a bath temperature of 95° C. According to GLC analysis, the residue (242.2 g) contains 44.1% of diethyl 5-ethylpyridine-2,3-dicarboxylate, which corresponds to a yield of 42.6% of theoretical, based on the sodium salt of diethyl 2-oxosuccinate used.

EXAMPLE 5

740 g of toluene, 250 g of water, and 117 g of (32%) hydrochloric acid are initially introduced into a 2 liter round-bottom flask, and 209.5 g of the sodium salt of diethyl 2-oxosuccinate is added at 25° C. within 5 minutes. After a reaction time of 1 hour at 25° C., phase separation takes place.

The organic phase (922.3 g) is heated to 30° C. after addition of 9.4 g of p-toluenesulfonic acid, and 141.8 g of 2-ethylacrolein oxime (purity 90.8%) is added dropwise at this temperature within 15 minutes. After a reaction time of 7 hours at 83° to 90° C., the mixture is allowed to cool to room temperature, the organic phase (1059.2 g) is separated from the water phase and washed three times with 300 g of water each time.

The organic phase after washing (1024.0 g) is freed of the solvent in the vacuum of an aspirator at a bath temperature of 95° C. According to GLC analysis, the residue (253.3 g) contains 47.2% of diethyl 5-ethylpyridine-2,3-dicarboxylate, which corresponds to a yield of 47.6% of theoretical, based on the sodium salt of diethyl 2-oxosuccinate used.

EXAMPLE 6

740 g of toluene, 250 g of water, and 117 g of (32%) hydrochloric acid are initially introduced into a 2 liter round bottom flask, and 209.5 g of the sodium salt of diethyl 2-oxosuccinate is added at 25° C. within 5 minutes. After a reaction time of 1 hour at 25° C., phase separation takes place.

The organic phase (922.8 g) is heated to 85° C. after addition of 9.4 g of p-toluenesulfonic acid, and 141.8 g of 2-ethylacrolein oxime (purity 90.8%) is added dropwise at this temperature within 15 minutes. After a reaction time of 7 hours at 84° to 90° C., the mixture is allowed to cool to room temperature, the organic phase (1062.1 g) is separated from the water phase and washed three times with 300 g of water each time.

The organic phase after washing (1020.6 g) is freed of the solvent in the vacuum of an aspirator at a bath temperature of 95° C. According to GLC analysis, the residue (249.6 g) contains 44.4% of diethyl 5-ethylpyridine-2,3-dicarboxylate, which corresponds to a yield of 44.2% of theoretical, based on the sodium salt of diethyl 2-oxosuccinate used.

We claim:

1. A process for the preparation of esters of 5-alkyl-pyridine-2,3-dicarboxylic acid comprising reacting 2-oxosuccinic acid esters with 2-alkylacrolein oximes in the presence of at least one acid catalyst.

2. The process of claim 1 wherein said catalyst is selected from the group consisting of strong inorganic acids, organic sulfonic acids, and organic carboxylic acids.

3. The process of claim 2 wherein said catalyst is selected from the group consisting of sulfuric acid, hydrochloric acid, methanesulfonic acid, p-toluene sulfonic acid and acetic acid.

4. The process of claim 3 wherein said catalyst is p-toluene-sulfonic acid.

5. The process of claim 1 wherein said catalyst is present in an amount of 0.01 to 0.2 moles per mole of said acid esters.

6. The process of claim 5 wherein said catalyst amount is 0.05 to 0.1 mole of said catalyst per mole of said acid esters.

7. The process of claim 1 wherein said reaction is carried out in the presence of an inert solvent.

8. The process of claim 7 wherein said solvent is selected from the group consisting of alcohols, esters, halogenated hydrocarbons, and aromatic hydrocarbons.

9. The process of claim 8 wherein said solvent is selected from the group consisting of butanol, ethylene glycol, ethyl acetate, chloroform, carbon tetrachloride, benzene, toluene, and xylene.

10. The process of claim 7 wherein said acid is present in said solvent in a concentration of 10% to 50% by weight.

11. The process of claim 1 wherein said acid and said oximes are present in a molar ratio of 1:2 to 2:1.

12. The process of claim 1 wherein said oxime has an alkyl group having 1 to 10 carbon atoms.

13. The process of claim 1 wherein said reaction is carried out at a reaction temperature of 50° to 150° C.

14. The process of claim 13 wherein said reaction temperature is 80° C. to 100° C.

15. The process of claim 1 wherein said reaction takes place for 4 to 10 hours.

* * * * *